(12) United States Patent  (10) Patent No.: US 7,909,606 B2
Marcello  (45) Date of Patent: Mar. 22, 2011

(54) METHOD FOR PLANNING AND PERFORMING DENTAL TREATMENTS

(76) Inventor: Marchesi Marcello, Modena (IT)

(*) Notice: Subject to any disclaimer, the term of this patent is extended or adjusted under 35 U.S.C. 154(b) by 109 days.

(21) Appl. No.: 11/962,679

(22) Filed: Dec. 21, 2007

(65) Prior Publication Data

US 2008/0153061 A1  Jun. 26, 2008

(30) Foreign Application Priority Data

Dec. 21, 2006 (IT) .............................. MO2006A0417

(51) Int. Cl.
A61C 5/00 (2006.01)
(52) U.S. Cl. ...................................................... 433/215
(58) Field of Classification Search .................. 433/204, 433/215, 216
See application file for complete search history.

(56) References Cited

U.S. PATENT DOCUMENTS

2005/0089822 A1* 4/2005 Geng ............................ 433/215

FOREIGN PATENT DOCUMENTS

DE 10 2005 034 803 A1 3/2006

OTHER PUBLICATIONS

Partial European Search Report dated Apr. 18, 2008.

* cited by examiner

*Primary Examiner* — Cris L Rodriguez
*Assistant Examiner* — Eric Rosen
(74) *Attorney, Agent, or Firm* — Browdy and Neimark, PLLC

(57) ABSTRACT

Method for planning and performing dental treatments including an acquisition phase of a set of data relating to the position, to the conformation and to the dimension of at least one site inside the oral cavity of a patient who has to undergo a dental treatment and relating to the conformation of at least one portion of the patient's face; a design phase of a virtual prototype of at least one dental prosthesis that can be fitted at the site during the treatment, starting from the set of data and by means of a software program implemented on a computer; a determination phase, by means of the software program and starting from the set of data and from the virtual prototype of the dental prosthesis, of at least one virtual model suitable for visually reproducing the portion of the face following the fitting of the dental prosthesis; a preparation phase of the site by means of a dental instrument, with the assistance of the software and starting from the virtual prototype of the dental prosthesis and from the virtual model before the installation and the manufacture of the dental prosthesis.

24 Claims, 4 Drawing Sheets

METHOD FOR PLANNING AND PERFORMING DENTAL TREATMENTS

FIELD OF THE INVENTION

This invention relates to a method for planning and performing dental treatments.

BACKGROUND OF THE INVENTION

In the dental field, it is known to carry out the preliminary planning of a treatment aimed, for example, at regenerating bone and periodontal tissues, at the manufacture and at the fitting of dental implants and prostheses, at performing reconstructive operations of a conservative type, at achieving a more effective masticatory occlusion and dynamics or, simply, a better structural and/or aesthetic conformation of a patient.

Planning methods are known that comprise the acquisition of one or more images relating to the site to be treated and the subsequent processing of the images acquired by means of dedicated software of the CAD-CAM (Computer Aided Design and Manufacturing) type implemented on a computer.

With particular reference to the manufacture of dental prostheses, the image is first of all acquired of the area where the prosthesis is to be fitted and, if necessary, of the teeth adjacent and/or antagonist to this area.

The image of the prosthesis fitting site can be determined, for example, by means of digital photography, computerised tomography (CT), electronic scanning of a plaster model obtained starting from an impression of the patient's dental arch or using other different methods.

The dedicated software programs process such acquired image, if necessary supplementing such data with others provided at input and determine a virtual model of the prosthesis to be made.

The virtual model thus determined can afterwards be used to make the prosthesis by means of semi-automated or automated processes such as, for example, rapid prototyping processes or, alternatively, processes that comprise the use of a modelling unit, of the type of a milling unit or the like, to obtain the dental prosthesis starting from a block of material.

These known methods, however, are not without drawbacks and, in particular, they do not allow accurate preparation of the area where the dental treatment is to be fitted before the installation of the prosthesis itself.

In fact, the preparation of the fitting area is done manually by the health operator, on the basis of the indications provided during the planning phase and comprises, for example, the installation of osteointegrated implants and/or the machining of one or more teeth suitable for supporting the dental prosthesis.

The result therefore is a substantially imprecise preparation or, in any case, a preparation not totally in conformity with whatever is defined in the planning phase.

Another drawback of the known methods is that of not allowing a preliminary evaluation of the impact of a dental treatment on a patient's appearance.

Such known methods, in fact, though permitting a preventive analysis of a qualitative functional type on the result of the dental treatment, do not however permit an analysis of the possible effects on the appearance of the patient's face. The patient is not therefore in a position to totally assess the effects of the treatment and the health operator is not, if necessary, able to change the parameters of the treatment itself to upgrade aesthetic aspects.

OBJECT OF THE INVENTION

The main aim of the present invention is to provide a method for planning dental treatments that allows an accurate preparation of the area where the dental treatment is to be fitted before the installation of the dental prosthesis.

Within the scope of this technical aim, another object of the invention is to provide a method that allows the preliminary study of the impact of a specific dental treatment on the patient's appearance.

Another object of the present invention is to provide a method for planning dental treatments that allows the mentioned drawbacks of the prior art to be overcome within the ambit of a simple and rational solution which is easy and effective to use.

The above objects are all achieved by the present method for planning and performing dental treatments, comprising:

an acquisition phase of a set of data relating to the position, to the conformation and to the dimension of at least one site inside the oral cavity of a patient who has to undergo a dental treatment and relating to the conformation of at least one portion of the face of said patient;

a design phase of a virtual prototype of at least one dental prosthesis that can be fitted at said site during said treatment, starting from said set of data and by means of a software program implemented on a computer;

a determination phase, by means of said software program and starting from said set of data and from said virtual prototype of the dental prosthesis, of at least one virtual model suitable for visually reproducing said portion of the face following the fitting of said dental prosthesis;

a preparation phase of said site by means of a dental instrument, with the assistance of said software and starting from said virtual prototype of the dental prosthesis and from said virtual model, before the installation and the manufacture of said dental prosthesis.

BRIEF DESCRIPTION OF THE DRAWINGS

Further characteristics and advantages of the present invention will appear more evident from the description of a preferred but not exclusive embodiment of a method for planning and performing dental treatments, illustrated indicatively by way of non limiting example, in the attached drawings wherein.

DETAILED DESCRIPTION OF THE PREFERRED EMBODIMENT(S)

With particular reference to such figures, by 1 has been globally indicated a method for planning and performing dental treatments such as, for example, the regeneration operations of bone and periodontal tissues, the installation of dental implants and prosthesis or operations aimed at achieving a more effective masticatory occlusion and dynamics.

Figure 1:
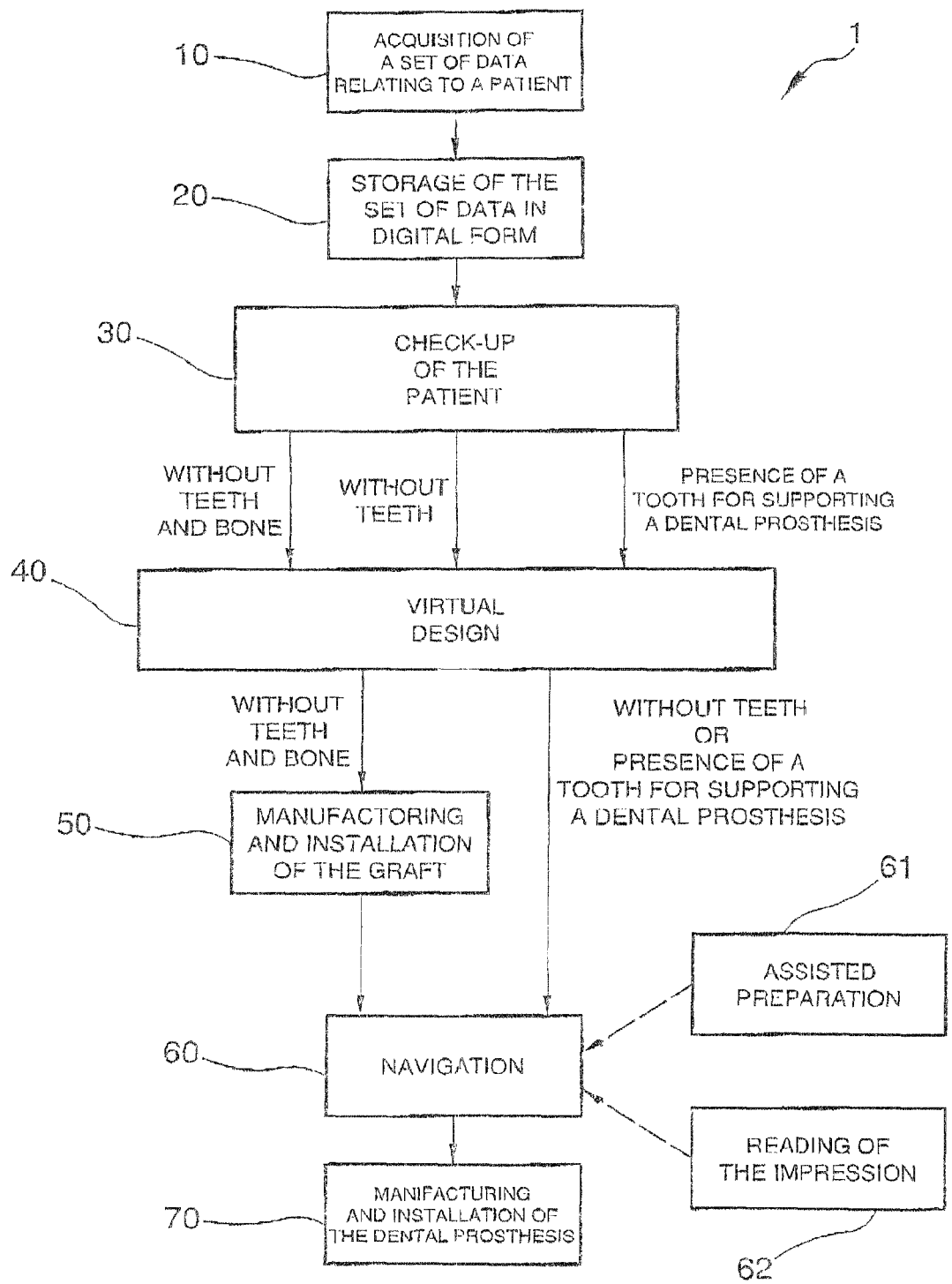
FIG. 1 is a general diagram that shows the method according to the invention.

As illustrated in FIG. 1, the method 1 comprises a preliminary acquisition phase 10 of a set of data relating to the position, to the conformation and to the dimension of a site inside the oral cavity of a patient who has to undergo a dental treatment.

In particular, the acquisition 10 can comprise the reading of a plurality of images of the site and, if necessary, of the teeth adjacent and/or antagonist to it by means of computerised tomography, by means of digital photography, by means of laser or white light scanning or, in general, by the electronic scanning of a plaster model obtained starting from an impression of the dental arch to be treated.

The use of different technologies suitable for acquiring such images of the site to be treated cannot however be ruled out.

The above set of data further comprises information relating to the conformation of at least one portion of the patient's face.

In particular, the above acquisition phase 10 can comprise the reading of a plurality of images of the patient's face, for example, by means of digital photography, computerised tomography or, alternatively, by means of the use of holographic recording techniques.

The use of different technologies suitable for acquiring such images of the patient's face cannot however be ruled out.

The acquisition 10 can comprise the reading of a plurality of images relating to different expressions of the patient's face.

The method 1 comprises the transduction of the images thus acquired in the above set of data, in a digital format, and a subsequent storage phase 20 of such set of digital data inside a storing unit operatively associated with a computer, of the personal computer type or the like.

A subsequent check-up phase 30 of the condition of the patient permits defining the type of necessary dental treatment.

In particular, it could occur that at the site where the prosthesis is to be fitted the patient is without teeth and bone enough to ensure the support of dental implants. In this case the dental treatment must comprise at least the partial regeneration of the bone and periodontal tissues, the installation of dental implants at the regenerated portion and the manufacture and fitting of at least one dental prosthesis.

It must be pointed out that in this description, by prosthesis is meant an artificial device for replacing a portion of a tooth, of a complete tooth or of several adjacent teeth of the type, for example, of crowns or bridges.

Alternatively, from the check-up phase 30, it could appear that the patient, at the site, does not have enough teeth to support a dental prosthesis. In this case, the dental treatment will comprise the installation of supporting dental implants at the site and the manufacture and fitting of at least one dental prosthesis.

Finally, the check-up phase 30 could show the partial absence of teeth at the site, along with the presence of at least one tooth suitable for supporting a dental prosthesis. In this case, the dental treatment will comprise the machining of the tooth or teeth suitable for supporting the dental prosthesis and the subsequent manufacture and fitting of the dental prosthesis itself.

The check-up phase 30 can be performed by a health operator directly on the patient or, advantageously, can be performed on a virtual model suitable for visually reproducing the treatment fitting site and at least part of the patient's face.

This virtual model can be composed of a dimensional graphic representation obtained by means of a software program implemented on the above computer, which representation is processed using the set of stored digital data.

The method 1 then comprises a design phase 40 of a virtual prototype of the dental prosthesis and, if necessary, of a graft suitable for regenerating the bone and periodontal tissues, starting from the above set of stored digital data and by means of a software program implemented on a computer.

Figure 2:
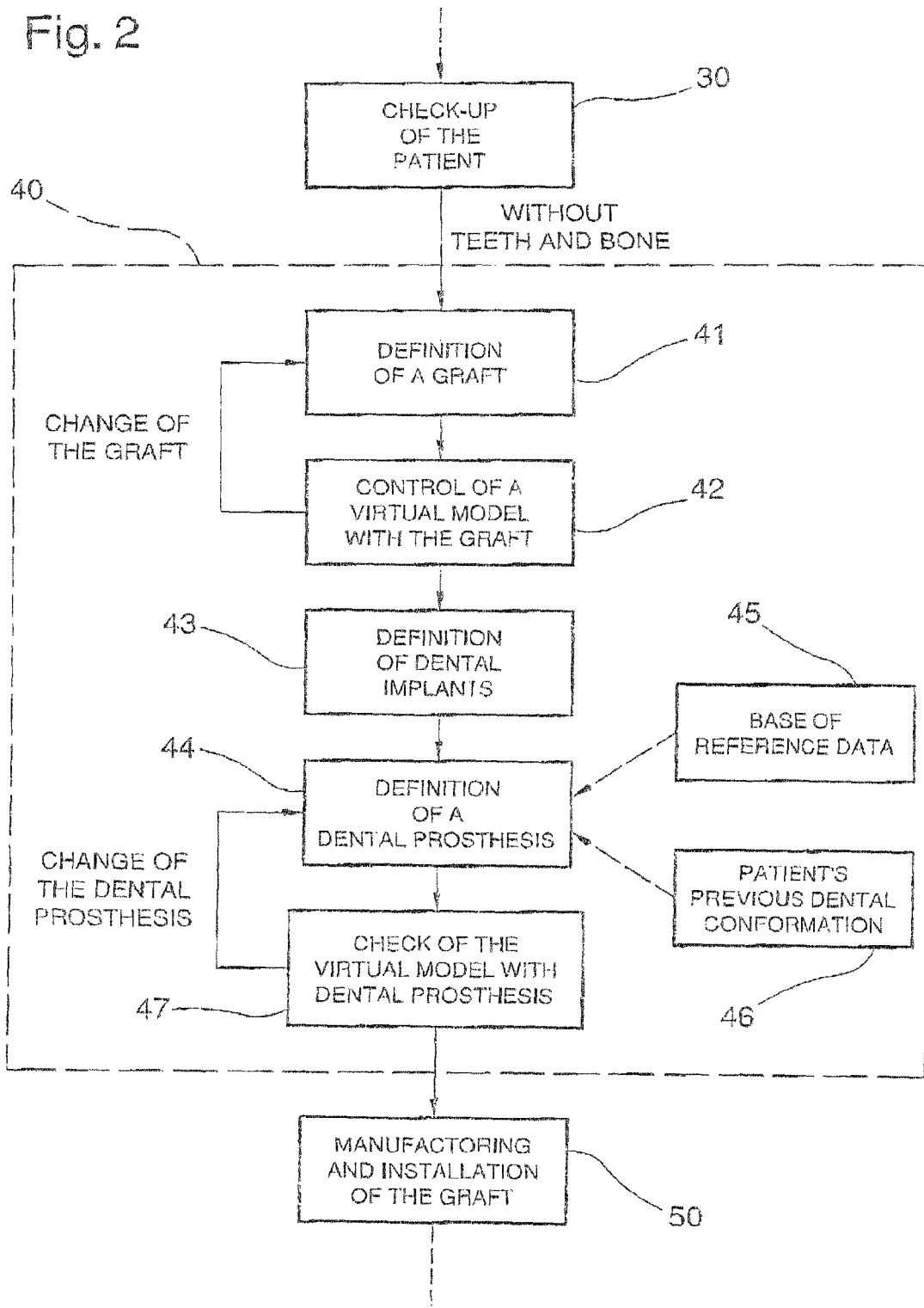
FIGS. 2, 3 and 4 are diagrams that show the main steps of a planning phase of the method according to the invention in relation to different types of dental treatment.

With specific reference to the case of the absence at the site of enough teeth and bone to ensure the support of dental implants, the design phase 40 can be schematised as illustrated in FIG. 2.

In particular, the design phase 40 comprises a first definition phase 41 of a virtual prototype of at least one graft for the guided regeneration of bone and/or periodontal tissues.

This first definition phase 41 can comprise a supplementary definition phase of a device for the controlled expansion of the soft tissues, installable at the site and suitable for creating the room required for the subsequent fitting of the graft.

The definition of this expansion device, which is of the type of a balloon or the like, makes it perfectly adaptable to the particular site to be treated and to the specific type of dental treatment.

A control phase 42 follows in which is displayed a three-dimensional graphic representation of a virtual model of the patient's face with the graft fitted. The virtual model is determined by means of the above software program and using the set of stored digital data and the virtual prototype of the graft.

The design phase 40 can comprise the change of the virtual prototype of the graft after the control phase 42 and, therefore, a further definition phase 41. The change of the virtual prototype of the graft can be repeated, until a condition is reached considered perfect by the health operator.

The design phase 40 also comprises a second definition phase 43 of a virtual prototype of one or more dental implants suitable for supporting a dental prosthesis.

Subsequently, a third definition phase 44 of a virtual prototype of the dental prosthesis to be installed at the site to be treated is considered.

The virtual prototype of the dental prosthesis can be defined starting from one or more virtual samples selected from a base of reference data 45 or, alternatively, it can be defined starting from one or more virtual samples, of the digital photo, scanned mold or other type, suitable for reproducing the patient's previous dental conformation, schematically illustrated with the block 46 in FIG. 2.

The design phase 40 comprises a check phase 47 in which a three-dimensional graphic representation is displayed of a virtual model of the patient's face with the dental prosthesis installed. The virtual model is obtained by means of the above software program and starting from the set of stored digital data and from the virtual prototype of the prosthesis.

During the check phase 47, a health operator assesses the functional aspects such as, for example, the position and the conformation of the dental prosthesis for a perfect occlusion during mastication and, usefully, performs a preliminary analysis of the aesthetic impact of the dental prosthesis on the patient's face. The analysis of the aesthetic impact concentrates on the face and on the aesthetic changes in the region of the lower lip and/or the upper lip.

The design phase 40 can comprise changing the virtual prototype of the dental prosthesis following the check phase 47 and, therefore, a further definition phase 44. The changing of the virtual prototype of the prosthesis is repeatable until a condition is reached considered optimal by the health operator.

Both the control phase 42 and the check phase 47 can comprise the display of different three-dimensional graphic representations of the virtual model relating to different facial expressions of the patient.

As shown in FIG. 1, and always with reference to the absence of enough teeth and bone to ensure the support of dental implants, after the design phase 40 a manufacturing and installation phase 50 is considered for the manufacture and installation of the graft and, if necessary, of the device for the controlled expansion of the soft tissues.

The graft can be made using automated rapid prototyping processes or other processes of known type.

Subsequently, the method 1 comprises a navigation phase 60 of the patient's oral cavity, which precedes a manufacturing and installation phase 70 of the dental prosthesis.

In particular, the navigation phase 60 comprises a preparation phase 61 of the fitting site of the dental prosthesis by means of a dental instrument. The preparation phase 61 is assisted by the software which processes, starting from the virtual prototype of the prosthesis and the virtual model of the patient's face, a three-dimensional graphic representation of the relative position of the handpiece with respect to the site to be prepared and with respect to the patient's upper or lower arch. In point of fact, during the preparation phase 61 of a site, the method according to the invention comprises the control of the quantity of material removed using the instrument from the tooth, from the pillar of the osteointegrated implant or from the area of bone tissue where the osteointegrated implant is to be installed.

The preparation phase 61 can comprise the assisted installation of the dental implants and/or the assisted machining of at least one tooth suitable for supporting the dental prosthesis.

The navigation phase 60 comprises a reading phase 62 of a virtual impression of the site prepared for the fitting of the prosthesis, of the type of a three-dimensional image or the like, performed at the same time as the preparation phase 61 and always using the dental instrument.

The manufacturing and installation phase 70 can comprise, for example, the control of a modelling unit, of the type of a milling unit or the like, to obtain the dental prosthesis starting from a block of material.

The use cannot be ruled out however of different manufacturing processes such as, for example, substantially automated rapid prototyping processes.

Figure 3:
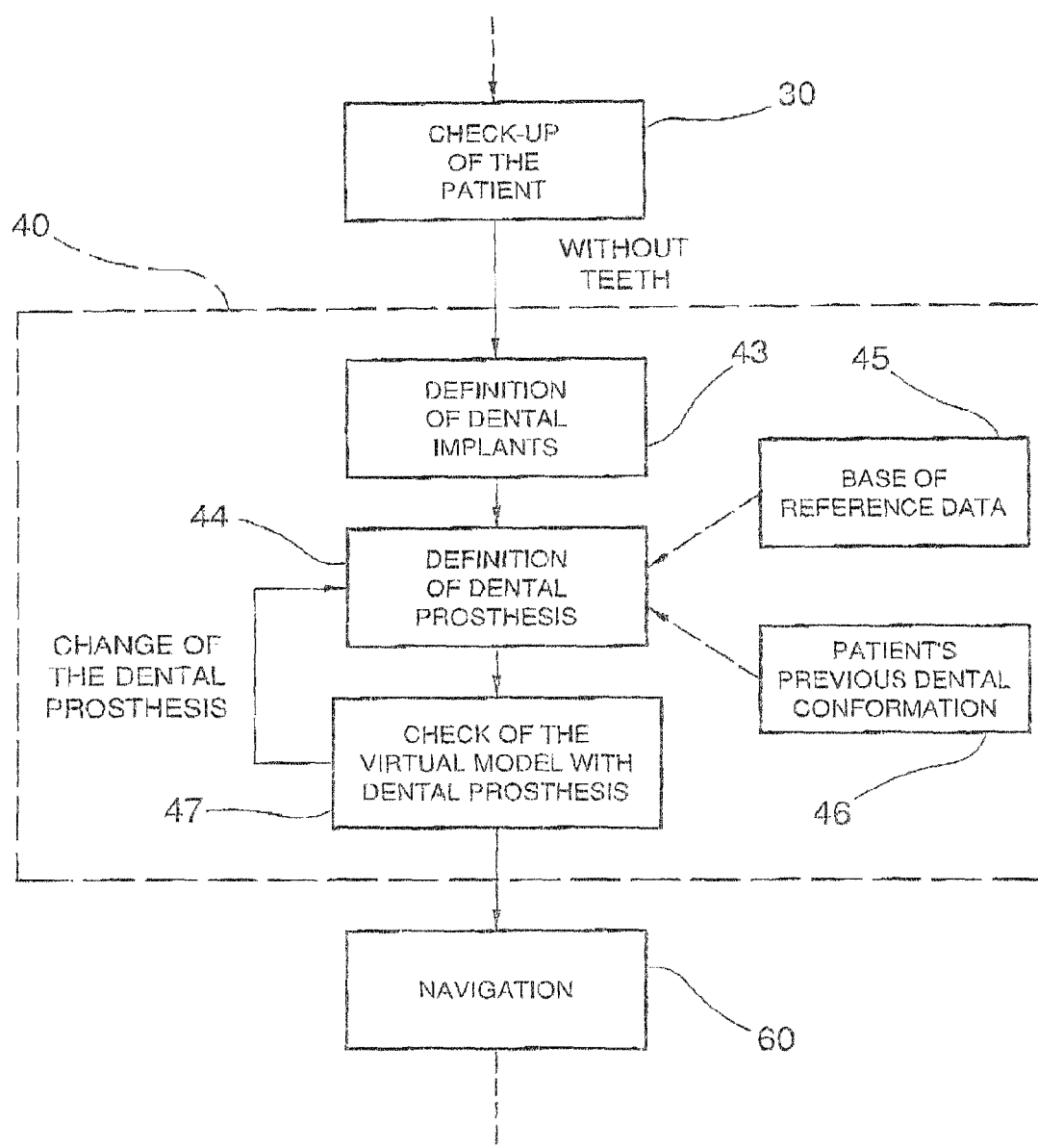

With specific reference to the case in which the patient has enough bone at the site to ensure the support of dental implants but is without teeth, the design phase 40 can be schematised as shown in FIG. 3.

In particular, following the check-up phase 30 of the patient's condition, the second definition phase 43 is performed of a virtual prototype of the dental implants. The design phase 40 then continues in the same way as described above in the case of the absence of bone and teeth and, after the check phase 47, the navigation phase 60 is carried out.

Figure 4:
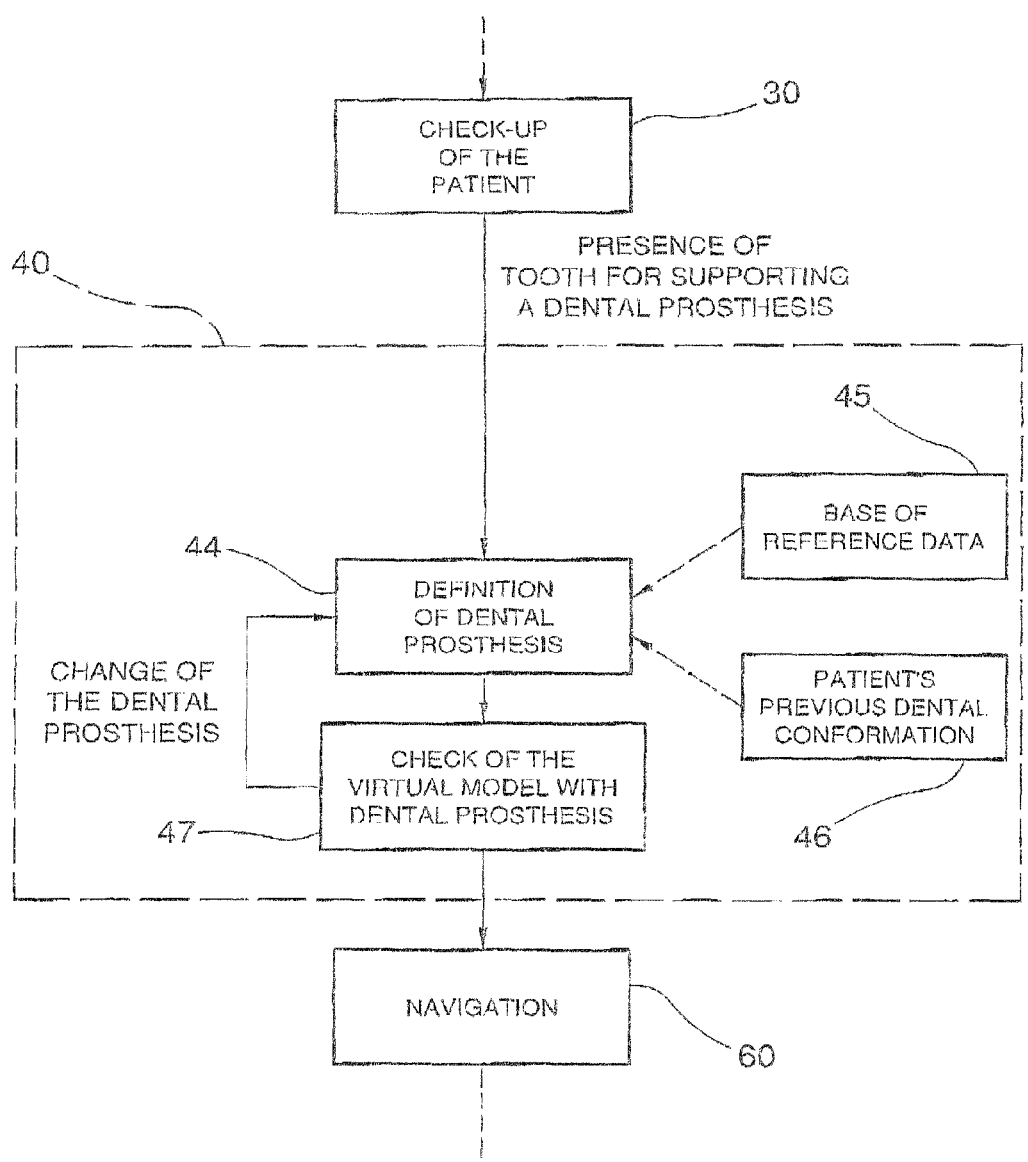

With specific reference to the case in which the patient has enough bone and teeth at the site to ensure the support of the dental prosthesis, the design phase 40 can be schematised as shown in FIG. 4.

In particular, after the check-up phase 30 of the patient's condition, the third definition phase 44 is performed of a virtual prototype of the dental prosthesis. The design phase 40 and the method 1 then continue in the same way as described above in the case of the absence of teeth and the existence of enough bone to ensure the support of dental prostheses.

It has in fact been found how the described invention achieves the proposed objects and in particular, the fact is underlined that the navigation phase, in particular the assisted preparation phase, permits a careful preparation of the site before the installation of the dental prosthesis.

Another advantage is represented by the processing of a virtual model of the patient's face, which allows the preliminary study of the effect of a specific dental treatment on the appearance of the patient's face.

The invention thus conceived is susceptible of numerous modifications and variations, all of which falling within the scope of the inventive concept. Furthermore all the details may be replaced by other elements which are technically equivalent.

In practice, the materials used as well as the contingent shapes and dimensions may be any according to requirements without because of this moving outside the protection scope of the following claims.

The invention claimed is:

1. Method for planning and performing dental treatments, comprising:

acquiring a set of data representing a position, a shape and dimensions of at least one site inside the oral cavity of a patient who has to undergo a dental treatment and representing the shape of at least one portion of an outer surface of the face of said patient in a plurality of different facial expressions, wherein said step of acquiring comprises transduction of said acquired set of data into a set of digital data;

subsequently storing said set of digital data inside a storing unit operatively associated with a computer;

conducting a check-up of the condition of the patient and determining the type of necessary dental treatment, wherein said check-up is performed on a first virtual model suitable for visually reproducing said at least one site and the at least one portion of the outer surface of the patient's face;

designing a prosthesis virtual prototype of a dental prosthesis that can be fitted at said at least one site during said treatment, and determining a second virtual model suitable for visually reproducing said at least one portion of the outer surface of the patient's face after said dental prosthesis is installed in the patient's oral cavity, using a software program implemented on said computer that starts from said set of digital data and processes said digital data to build said prosthesis virtual prototype and said second virtual model;

preparing said at least one site using a dental instrument and said software program and using said prosthesis virtual prototype of the dental prosthesis and using said second virtual model, before said dental prosthesis is manufactured and installed; and using said software program to perform the following steps:

processing, using said prosthesis virtual prototype of the dental prosthesis and using said second virtual model, a three-dimensional graphic representation of the relative position of said dental instrument with respect to the at least one site to be prepared, and controlling a quantity of material removed using said dental instrument from a tooth, from a pillar of an osteointegrated implant or from an area of bone tissue where an osteointegrated implant is to be installed;

wherein said method further comprises:

reading a virtual impression of said at least one site prepared for the fitting of said dental prosthesis, wherein said virtual impression is in the form of a three-dimensional image, said step of reading being performed at the same time as said step of preparing using said dental instrument; and manufacturing and installing said dental prosthesis.

2. Method according to claim 1, wherein said step of designing comprises checking the virtual model of said at least one portion of the outer surface of the patient's face with said dental prosthesis by displaying the virtual model of the at least one portion of the outer surface of the patient's face with the dental prosthesis installed.

3. Method according to claim 2, comprising changing said virtual prototype of the dental prosthesis after the step of conducting the check-up of the condition of the patient.

4. Method according to claim 2, wherein said step of checking comprises displaying different three-dimensional graphic representations of said first virtual model representing different facial expressions of said patient.

5. Method according to claim 1, wherein said step of designing comprises designing a virtual prototype of at least one graft for the guided regeneration of at least one of bone and periodontal tissues.

6. Method according to claim 5, further comprising, after said step of designing comprises displaying a three-dimensional graphic representation of the virtual model of the at least one portion of the outer surface of the patient's face with the at least one graft fitted in the patient's oral cavity.

7. Method according to claim 6, further comprising changing said virtual prototype of the at least one graft after said step of displaying the three-dimensional graphic representation of the virtual model of the at least one portion of the outer surface of the patient's face with the at least one graft fitted in the patient's oral cavity.

8. Method according to claim 6, wherein said step of displaying a three-dimensional graphic representation of the second virtual model of the at least one portion of the outer surface of the patient's face with the at least one graft fitted in the patient's oral cavity comprises displaying different three-dimensional graphic representations of said second virtual model representing different facial expressions of said patient.

9. Method according to claim 5, wherein said step of designing further comprises designing a device for the controlled expansion of the soft tissues, installable at said at least one site and suitable for creating room required for the subsequent fitting of said at least one graft.

10. Method according to claim 5, further comprising a step of manufacturing and installing said at least one graft.

11. Method according to claim 10, wherein said step of manufacturing and installing said dental prosthesis comprises controlling at least one modelling unit for the dental prosthesis, said at least one modelling unit comprising a milling unit of a block of material.

12. Method according to claim 11, wherein said step of manufacturing and installing said dental prosthesis further comprises a substantially automated rapid prototyping process.

13. Method according to claim 1, wherein said step of designing further comprises designing an implant virtual prototype of a dental implant supporting said dental prosthesis.

14. Method according to claim 1, wherein said step of designing further comprises designing the prosthesis virtual prototype of said dental prosthesis starting from at least one virtual sample selected from a base of reference data.

15. Method according to claim 1, wherein said step of designing further comprises designing the prosthesis virtual prototype of said dental prosthesis starting from at least one virtual sample suitable for reproducing a previous dental conformation of said patient.

16. Method according to claim 1, wherein said step of conducting a check-up comprises displaying a three-dimensional graphic representation of said first virtual model.

17. Method according to claim 1, wherein said step of acquiring comprises reading of at least one image of said at least one site.

18. Method according to claim 1, wherein said step of acquiring comprises reading of at least one image of said at least one portion of the outer surface of the patient's face.

19. Method according to claim 1, wherein said step of acquiring comprises reading of a plurality of images of said at least one portion of the outer surface of the patient's face representing different face expressions of said patient.

20. Method according to claim 1, wherein said step of acquiring comprises using holographic recording for acquiring the set of data.

21. Method according to claim 1, wherein said step of acquiring comprises using computerized tomography for acquiring the set of data.

22. Method according to claim 1, wherein said step of acquiring comprises using one of laser scanning or white light scanning for acquiring the set of data.

23. Method according to claim 1, wherein said step of preparing said at least one site comprises an assisted installation of said dental implants.

24. Method according to claim 1, wherein said step of preparing said at least one site comprises an assisted machining of at least one tooth suitable for supporting said dental prosthesis.

* * * * *